(12) United States Patent
Camu

(10) Patent No.: US 7,320,780 B2
(45) Date of Patent: Jan. 22, 2008

(54) STERILISING UNIT

(76) Inventor: Patrice Camu, Le Clos des Cedres 17, rue d'Ottersthal, F-67700 Saverne (FR)

( * ) Notice: Subject to any disclaimer, the term of this patent is extended or adjusted under 35 U.S.C. 154(b) by 745 days.

(21) Appl. No.: 10/473,951

(22) PCT Filed: Mar. 22, 2002

(86) PCT No.: PCT/FR02/01014

§ 371 (c)(1),
(2), (4) Date: Mar. 30, 2003

(87) PCT Pub. No.: WO02/080988

PCT Pub. Date: Oct. 17, 2002

(65) Prior Publication Data

US 2004/0105797 A1   Jun. 3, 2004

(30) Foreign Application Priority Data

Apr. 9, 2001   (FR) .................................. 01 04875

(51) Int. Cl.
*A61L 2/07* (2006.01)
(52) U.S. Cl. .................. 422/300; 422/26; 422/302; 414/331.12; 221/222
(58) Field of Classification Search ................ 422/295, 422/297, 307; 414/331.12; 221/222, 297
See application file for complete search history.

(56) References Cited

U.S. PATENT DOCUMENTS 3,606,995 A    9/1971 Hemel
4,077,528 A *  3/1978 Santen ........................ 414/152
5,619,908 A    4/1997 Catelli et al.

FOREIGN PATENT DOCUMENTS

FR    2 172 816 A    10/1973
FR    2172816    *    10/1973
WO    WO8606354    *    11/1986

* cited by examiner

*Primary Examiner*—E. Leigh McKane
(74) *Attorney, Agent, or Firm*—Egbert Law Offices

(57) ABSTRACT

A sterilizing unit for food, pharmaceutical and like products, packaged in rigid or soft containers, includes at least an autoclave adapted to receive, through at least an access door and through a loading/unloading unit, at least a container wherein are arranged packages. Advantageously, the autoclave is vertically arranged and includes internally vertical conveying device designed to be subjected, by a motoring mechanism for loading and unloading them in a step-by-step forward movement through the access door(s) for containers in the form of shelves.

7 Claims, 1 Drawing Sheet

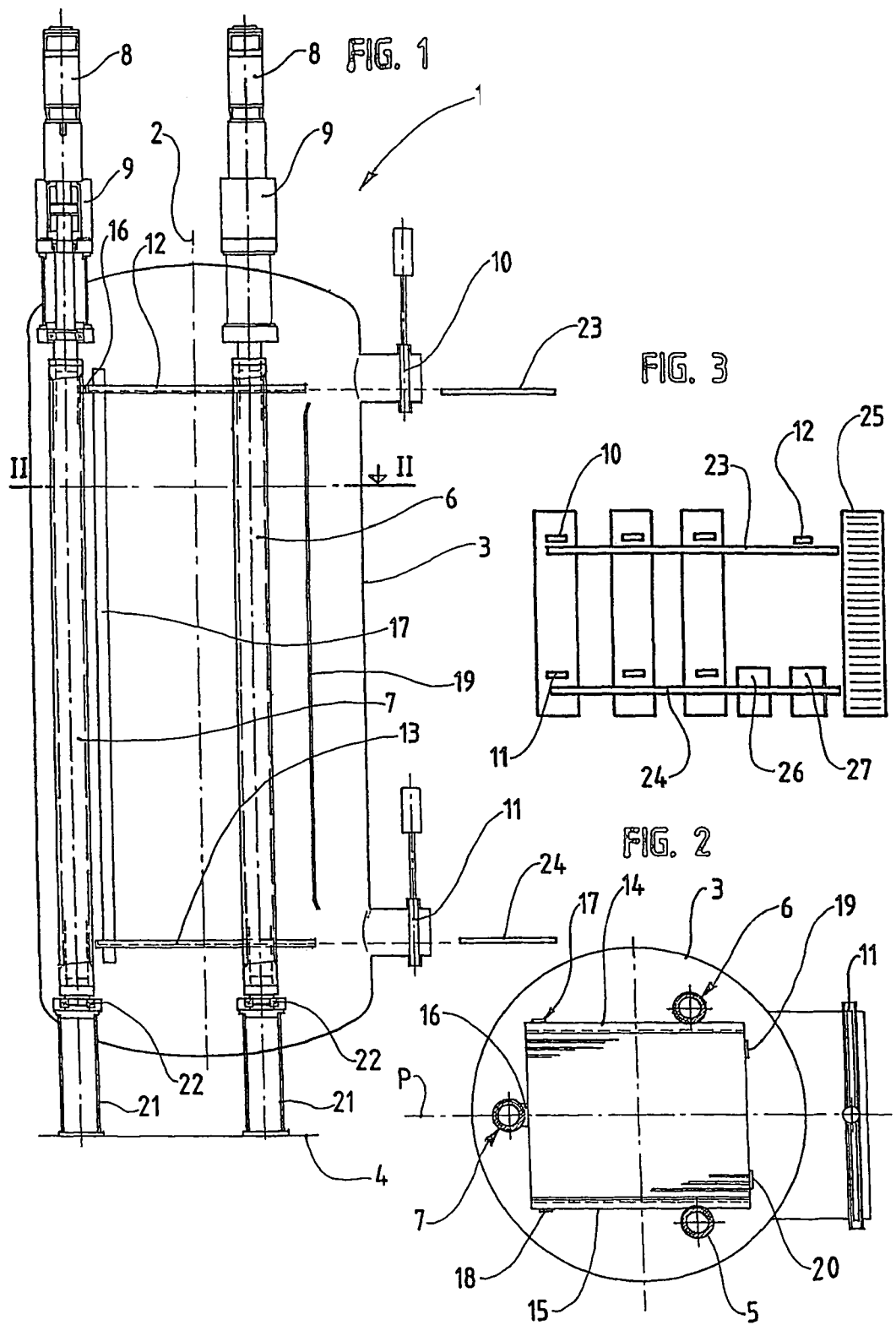

US 7,320,780 B2

STERILISING UNIT

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to a sterilizing unit for food, pharmaceutical products and the like, packaged in rigid or soft containers, comprising at least an autoclave designed capable of receiving, through at least one access door and by means of a loading-unloading unit, at least one container wherein said containers are arranged.

The invention relates to the field of sterilization of substances packaged in rigid containers, such as bottles, flasks, jars, or soft containers, such as soft thermally welded bags, within the framework of a production line for food, pharmaceutical, veterinary products or the like contained in such packages.

BACKGROUND OF THE INVENTION

Such sterilizing units are known within the framework of the agro-food or pharmaceutical production sites. A number of autoclaves are grouped into one or several sterilizing units after the food or pharmaceutical process, i.e. when the product is contained in its commercial package, before placing the label and placing it into cardboard boxes or plastic films, e.g. in the case of a traditional can.

Said autoclaves generally have an elongated cylindrical shape and are arranged horizontally. In order to optimize the operation of the industrial site considered, the autoclaves are arranged in parallel, side by side, so that their access doors, which are usually located at one of their ends, are aligned perpendicularly to a loading-unloading circuit in a loop.

Each autoclave is supplied, at the beginning of a cycle, with containers, e.g. pallets filled with containers of substances to be sterilized. Said supply is ensured by a loading unit and through adequate conveying means that can be, among others, a belt, a rail, a chain conveyer, or a cable-guided line. An older organization will implement pallet-bearing fork trucks.

Similarly, each autoclave is unloaded at the end of the cycle by an unloading unit, which can eventually be identical to said loading unit, through evacuating conveying means. Inside each autoclave, an adequate device allows circulating and positioning the various pallets, as occurs in cargo-planes, e.g. by means of cylindrical rolls.

The whole of these operations requires a fine synchronization between the operating cycles of the various autoclaves, the loading and unloading times, as well as the preparation and releasing times for the containers. Thus, the latter must, before sterilization, be loaded with products proceeding from the manufacturing halls, e.g. jars or bags, and, after sterilization, be emptied of said sterilized products, leaving for labeling, putting into cardboard boxes or films, then storage before shipping.

It should be stated that the sterilization cycle comprises thermal and mechanical actions. The thermal actions consist in subjecting the products, arranged in their container, furthermore clamped on adequate supports, to temperature-raising, and lowering cycles, said cycles being induced by means such as sending vapor into the chamber of the autoclave and, inversely, sending cold water showering the products.

The mechanical actions consist, during the sterilization phase, in generating vibrations, oscillations or turning upside down, of said products.

The looped circuit of the sterilization room does or not allow the passing ahead of containers, in order to optimize the waiting times before each autoclave. This organization has a number of drawbacks, some of which are directly related to the autoclaves:

Firstly, because of their horizontal arrangement, the autoclaves occupy a large floor space, both for themselves and for the related evolution area.

Secondly, the loading and unloading of said containers from a door located at the end of the autoclave assumes efficient proper horizontal displacement means, generally on the floor, as well as an optimization of the height, the width and the length of the various loads depending on the useful dimensions of these autoclaves. This means can be relatively complex and cumbersome.

Thirdly, the jacket of the loaded autoclaves should be designed capable of resisting, in addition to the temperature and pressure cycles, to the stresses generated by the weight of the load.

BRIEF SUMMARY OF THE INVENTION

To this end, the present invention relates to a sterilizing unit for food, pharmaceutical products and the like, packaged in rigid or soft, containers, comprising at least an autoclave designed capable of receiving, through at least one access door and by means of a loading-unloading unit, at least one container wherein said containers are arranged.

According to the invention, the autoclave is arranged vertically and includes, inside, vertical conveying means capable of being subjected, by means of suitable motor means, to a stepwise forward movement for their loading and unloading, through the access door or doors, with containers in the form of shelves designed capable of being loaded and unloaded into rigid or soft containers by said loading-unloading unit.

According to another feature of the invention, said vertical conveying means are comprised of at least three worms, at least two of which are located on both sides of the space for displacement of the containers with respect to a plane passing through the vertical axis of said autoclave and substantially through the median axis of the access door or doors, and at least one of which extends vertically on the side of this space for displacement of the containers opposite the one in front of said door or doors.

According to another feature of the invention, said container or containers are provided with resting rims designed capable of co-operating with the thread of the worms.

According to another feature of the invention, said containers are guided vertically through guiding rails extending parallel to the worm or worms.

According to another feature of the invention, both worms located on both sides of the space for displacement of the containers have inverted pitches, so as to be capable of being subjected to a rotation in opposite direction, determined so as to push the containers into contact with the third worm.

According to another feature of the invention, said vertical conveying means are designed capable of entirely bearing the weight of the containers with products to be sterilized and to transmit it to the floor through bases.

According to another feature of the invention, said sterilizing unit is provided with means for putting the containers into oscillation.

Advantageously, the means for putting said containers into oscillation are comprised of at least one of the worms, which is subjected to an alternate rotation of a determined magnitude.

The invention will be better understood when reading the following description, with reference to the attached drawing, which relates to one embodiment.

BRIEF DESCRIPTION OF THE SEVERAL VIEWS OF THE DRAWINGS

FIG. 1 is a schematic, vertical cross-sectional view of an autoclave of a sterilizing unit according to the invention.

FIG. 2 is a schematic cross-sectional view according to II-II of FIG. 1.

FIG. 3 is a schematic elevational view of the means for loading-unloading the autoclave of the sterilizing unit.

DETAILED DESCRIPTION OF THE INVENTION

As shown in the figures of the attached drawing, the present invention relates to the field of the sterilizing units for food, pharmaceutical products or the like, packaged in rigid or soft containers, comprising at least one autoclave 1.

The latter, shown in vertical cross-section in FIG. 1 and in perpendicular cross-section in FIG. 2, is of a cylindrical type, the longitudinal axis 2 of its chamber 3 being vertical. Vertical conveying means, more particularly worms 5, 6, 7, as can be seen in FIG. 2, are arranged vertically within this chamber 3.

On these worms 5, 6, 7 act motor means allowing putting them into rotation in one direction or in the other, said motor means comprising e.g. an electric motor 9 associated with a reduction gear 9.

Preferably, two horizontally elongated doors 10, 11 are provided for in one and the same vertical alignment, laterally in the wall delimiting the chamber 3 of the autoclave 1. These doors are so dimensioned as to allow the passing through of the containers 12 during the handling, both for loading and unloading. Such a container 12, in this case a shelf, has been shown in cross-section in FIG. 1, in the upper portion of the autoclave 1 in front of an upper door. Similarly, another container 13, in this case also a shelf, is shown in cross-section in the lower portion of the autoclave in front of a lower door 11, said lower door 11 being also shown in FIG. 2.

At least two worms 5, 6 are arranged on both sides of the shelf-displacing space 12, 13 with respect to a vertical plane P passing through the vertical axis of said autoclave 1 and substantially through the median axis of its door or doors 10, 11, said vertical plane P corresponding to the cross-section plane of FIG. 1. Furthermore, at least a third worm 7 is preferably located in said plane P, on the side, with respect to this shelf-displacing space 12, 13, opposite the one of said doors 10, 11.

In order to ensure their positioning, the shelves or containers 12, 13 are provided, at their periphery, with resting rims 14, 15, 16 designed capable of cooperating with the threads of the worms 5, 6, 7.

With a view to ensuring a guiding and an optimal positioning of the shelves 12, 13 during the handling operations, it can be advantageous to surround the stop represented by the worm 7 by two vertical side guiding rails 17, 18 separated by a distance equivalent to the width of a shelf 12, resting rims 14, 15 included, increased by the expected backlash.

Similarly and in order to ensure a guiding and an optimal positioning of tile shelves 12, 13 during the vertical positioning operations inside the chamber 3, it can be advantageous to arrange at least one vertical guiding rail 19, 20 located, with respect to the space for the movement of these shelves 12, 13, on the side of the access doors 10, 11. This or these vertical guiding rails 19, 20 are aimed, among others, at keeping the resting rim 16 of the shelf 12, 13 resting on the thread of the worm 7. Of course, said vertical guiding rails 19, 20 extend in a limited way, within the section of the chamber 3 that is free of any opening of doors, in order not to disturb or impede the passing through of the containers 12, 13.

Both worms 5, 6, located on both sides of the space for the movement of the shelves, as described above, advantageously have inverted pitches and a rotation in opposite direction is imparted to them, which results into pushing the shelves 12, 13 into contact with the third worm 7 located as described above.

Said worms 5, 6, 7 can be mounted, through bearings 22 allowing in particular the axial forces, on bases 21 emerging under the autoclave 1, in order to rest on the floor. These worms 5, 6, 7 therefore bear entirely the weight of the containers with products to be sterilized.

The previously mentioned loading-unloading means comprise at least conveyers 23, 24 extend horizontally in front of the access doors 10, 11 of the autoclaves 1, said sterilizing unit is comprised of. Said means are integrated in a more complex handling circuit, schematically shown in FIG. 3.

When, according to an exemplary embodiment, the shelves 12, 13 with products to be sterilized are loaded through the upper door 10 and the unloading occurs through the lower door 11, the handling and conveying operations are as follows: the shelves 12, 13 with products to be sterilized are loaded onto a loading station 27; then reach, through an elevator 25, an upper conveyer 23, before being inserted, through said upper door 10, into the autoclave 1 during the loading cycle. Once the sterilization cycle is completed, said shelves 12, 13 are removed from this autoclave 1 through a lower door 11 and reach an unloading station 26 by means of a lower conveyer 24.

Thus, the shelves 12 are inserted one after another through the upper door 10, from the upper conveyer 23. A proper rotation of the worms 5, 6, 7 lowers them by a distance equivalent to the height of a loaded shelf, increased with a safety interval, which is accurately obtained by a stepwise rotation control. The operation continues until the chamber 3 has been filled. To empty it, either the operation can be reversed or continued by using the lower door 11. The above operations can obviously be inverted, by operating from the lower door 11 and by using either said lower door 11 or the upper door 10 to unload.

Having one or several intermediate doors allows having several locations for a simultaneous loading, each rotation of the worms allowing lowering or raising by an identical distance one or several piles of shelves 12 within the autoclave 1, which allows to considerably reduce the handling times on high autoclaves.

Said autoclave 1 can authorize the putting into oscillation of the shelves 12, 13, this kind of motion allowing improving the thermal effects of the sterilization cycle. For example, at least one of the worms 5, 6, 7 can be caused to alternately rotate in one direction, than in the opposite direction, according to a determined magnitude. This results into alternately inclining the shelves in one direction, then in the other direction. A maximum inclination compatible with the geometry of the mechanical parts entering into contact should be respected.

In order to cool down the shelves 12 when necessary during a sterilization cycle, the chamber 3 can be provided with vertical spraying ramps, not shown here.

I claim:

1. A sterilizing apparatus comprising:
   an autoclave having a vertical longitudinal axis, said autoclave having at least one access door;
   a vertical conveying means positioned on an interior of said autoclave;
   at least one container received by said vertical conveying means through the access door, said vertical conveying means for moving the container vertically within said autoclave;
   a motor means cooperative with said vertical conveying means for selectively rotating said vertical conveying means in a stepwise manner, said vertical conveying means comprising a pair of worm gears arranged vertically on opposite sides of said access door and another worm gear extending vertically so as to be aligned with a center of said access door, said container being a shelf having a first side edge and a second side edge and an end edge and a forward edge, said first side edge being received by a thread of one of said pair of worm gears, said second side edge being received by a thread of the other of said pair of worm gears, said end edge received by a thread of said another worm gear; and
   a plurality of guide rails affixed to and extending vertically in said autoclave so as to contact said forward edge of the container so as to retain the container in said vertical conveying means and to guide the container vertically in said autoclave.

2. The sterilizing apparatus of claim 1, each of said edges of said shelf having a resting rim formed thereon suitable for cooperative receipt with the threads of the worm gears.

3. The sterilizing apparatus of claim 1, said pair of worm gears having inverted pitches, said motor means for rotating said pair of worm gears respectively in opposite directions so as to urge said shelf toward said another worm gear.

4. The sterilizing apparatus of claim 1, each of said worm gears having a base at a bottom thereof, said base suitable for supporting the worm gear above a floor.

5. The sterilizing apparatus of claim 1, further comprising:
   a loading and unloading means having one end positioned adjacent to said access door;
   a loading unit positioned adjacent an opposite end of said loading and unloading means; and
   an unloading unit positioned adjacent the opposite end of said loading and unloading means, said loading and unloading means for conveying the shelf to said access door and for evacuating the shelf from said access door.

6. The sterilizing apparatus of claim 1, said motor means for rotating the worm gears so as to oscillate the shelf upwardly and downwardly within said autoclave.

7. The sterilizing apparatus of claim 6, said motor means for alternately rotating the worm gears in different direction so as to oscillate the shelf for a desired distance.

* * * * *